United States Patent [19]

Takenaka et al.

[11] Patent Number: 4,694,110

[45] Date of Patent: Sep. 15, 1987

[54] PROCESS FOR PRODUCTION OF M-PHENOXYBENZYL ALCOHOL

[75] Inventors: Shinji Takenaka; Ryu Oi, both of Ohmuta, Japan

[73] Assignee: Mitsui Toatsu Chemicals, Inc., Tokyo, Japan

[21] Appl. No.: 861,414

[22] Filed: May 9, 1986

[30] Foreign Application Priority Data

May 13, 1985 [JP] Japan .................................. 60-99593

[51] Int. Cl.$^4$ ............................................ C07C 29/00
[52] U.S. Cl. .................................................... 568/638
[58] Field of Search ........................................ 568/638

[56] References Cited

FOREIGN PATENT DOCUMENTS 57-75947  5/1982  Japan .................................. 562/473
7806111  12/1978  Netherlands ......................... 568/638

OTHER PUBLICATIONS

Moroz et al., Russian Chemical Reviews, 43(8), (1974), 679-689.

Primary Examiner—James H. Reamer
Attorney, Agent, or Firm—Fisher, Christen & Sabol

[57] ABSTRACT

A process for producing m-phenoxybenzyl alcohol which comprises reacting chlorobenzene with m-hydroxybenzyl alcohol in the presence of a copper compound as a catalyst and a base, characterized in that chlorobenzene is added to a polar solvent having a higher boiling point than chlorobenzene, the amount of chlorobenzene being 0.05 to 4.0 times the weight of the polar solvent; at least one compound selected from alkali hydroxides, alkali carbonates and alkali bicarbonates is used as the base in an amount of 1.0 to 2.0 gram-equivalents per mole of m-hydroxybenzyl alcohol; and the reaction is carried out at a temperature of 140° to 200° C. while removing the generated water as an azeotrope with chlorobenzene.

3 Claims, No Drawings

PROCESS FOR PRODUCTION OF M-PHENOXYBENZYL ALCOHOL

BACKGROUND OF THE INVENTION

1. Field of the Invention

This invention relates to a process for the prodcution of m-phenoxybenzyl alcohol. More specifically, this invention relates to a process for producing m-phenoxybenzyl alcohol by the reaction of chlorobenzene with m-hydroxybenzyl alcohol.

2. Description of the Prior Art m-Phenoxybenzyl alcohol is a starting material for pyrethroid-type insecticides. In recent years, there has been an increasing demand for pyrethroid-type agricultural chemicals having low toxicity in order to reduce effects of agricultural chemicals on the human body, and m-phenoxybenzyl alcohol is accordingly in great demand. It is one great problem, therefore, in the development of agricultural chemicals to supply m-phenoxybenzyl alcohol at low costs.

Generally, the prior production of m-phenoxybenzyl alcohol relies on the chlorination or oxidation of the side chain of m-phenoxytoluene. This method, however, has the following defects.

(1) Chlorination of the side chain of m-phenoxytoluene

In the chlorination reaction of the side chain methyl group, a second chlorine addition occurs at the benzyl position to form a by-product. The desired product should therefore be separated and purified, and the hydrolysis in the subsequent step is complex.

(2) Oxidation of the side chain of m-phenoxytoluene

In the oxidation of the side-chain methyl group, the benzyl position is oxidized to the aldehyde or carboxylic acid without the reaction stopping at the stage of the alcohol. The resulting benzaldehyde or benzoic acid must be reduced to the desired product. Furthermore, at the time of oxidation, a large amount of potassium permanganate should be used, and the method is as complex as in (1).

Condensation of an m-chlorobenzoic acid ester or nitrile and a phenolate is also known as a method of producing m-phenoxybenzyl alcohol (French Patent No. 2,456,727). However, the m-chlorobenzoic acid ester or nitrile used in this invention is expensive, and the method cannot be industrially advantageous.

A method of obtaining m-phenoxybenzyl alcohol from m-hydroxybenzyl alcohol and bromobenzene using a copper dust as a catalyst was proposed (Japanese Laid-Open Patent Publication No. 61443/1973). The yield, however, is as low as about 80%. Since bromobenzene is higher in price than chlorobenzene, such a yield is industrially insufficient.

SUMMARY OF THE INVENTION

It is a first object of this invention to provide a process for producing m-phenoxybenzyl alcohol in a high yield by condensing m-hydroxybenzyl alcohol with chlorobenzene.

A second object of this invention is to provide a process by which m-phenoxybenzyl alcohol can be produced industrially at low costs owing to the use of chlorobenzene.

These objects are achieved in accordance with this invention by a process for producing m-phenoxybenzyl alcohol, which comprises reacting m-hydroxybenzyl alcohol with chlorobenzene in the presence of a copper compound catalyst and at least one compound selected from alkali hydroxides, alkali carbonates and alkali bicarbonates at a reaction temperature of 140° to 200° C., the chlorobenzene being charged into a polar solvent having a high boiling point than chlorobenzene in an amount 0.05 to 4.0 times the weight of the polar solvent, said alkaline compound being used in an amount of 1.0 to 2.0 gram-equivalents per mole of m-hydroxybenzyl alcohol, and the reaction being carried out while removing the generated water as an azeotrope with chlorobenzene.

The process for producing m-phenoxybenzyl alcohol in accordance with this invention is characterized in that chlorobenzene and a specific polar solvent are selected in a predetermined ratio, an alkali compound is used in a suitable proportion relative to m-hydroxybenzyl alcohol, and the reaction is carried out in this solvent in the presence of a copper compound at a suitable temperature while the generated water is removed out of the reaction system as an azeotrope with chlorobenzene. This enables m-phenoxybenzyl alcohol to be obtained in a high yield with good selectivity by using chlorobenzene without the need to use expensive bromobenzene.

DETAILED DESCRIPTION OF THE INVENTION

The alkali used in the process of this invention is selected, for example, from sodium hydroxide, potassium hydroxide, sodium carbonate, potassium carbonate, sodium bicarbonate and potassium bicarbonate. The alkali is usually required to be used in at least a theoretical amount with respect to m-hydroxybenzyl alcohol. Since, however, m-hydroxybenzyl alcohol is used as the starting material in the present invention, the use of a large amount of the alkali gives an increased amount of byproduct m-phenoxybenzylphenyl ether of the following formula

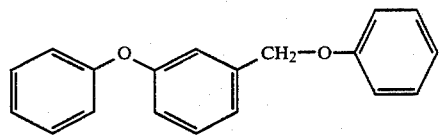

in addition to the desired m-phenoxybenzyl alcohol. When the alkali is used in an amount of about 2.0 gram-equivalents, the amount of the by-product formed is about 10%. Accordingly, in the present invention, the alkali compound is used in an amount of 1.0 to 2.0 gram-equivalents per mole of m-hydroxybenzyl alcohol.

The copper compound catalyst used in this invention may, for example, be a copper powder, a copper halide, or copper carbonate. Preferably, it is used in the form of a complex. In particular, an 8-hydroxyquinoline/copper complex known as a catalyst in the production of m-phenoxytoluene (Japanese Laid-Open Patent Publication No. 134,743/1984) is also preferred in this invention. When the 8-hydroxyquinoline/copper complex is used, its amount is preferably 0.5 to 5.0 moles % based on m-hydroxybenzyl alcohol. The 8-hydroxyquinoline/copper complex may be prepared in advance and then added to the reaction system. Alternatively, it is possible to form the complex in situ by adding a copper halide and 8-hydroxyquinoline to the reaction system.

In the practice of the process of this invention, m-hydroxybenzyl alcohol and chlorobenzene are charged into a polar solvent containing the alkali and the copper catalyst and having a higher boiling point than chlorobenzene, and are reacted at an elevated temperature while water formed at the time of forming an alkali metal salt of m-hydroxybenzyl alcohol.

In the present invention, the removal of water generated at the time of forming the alkali metal salt and the reaction temperature greatly affect the yield of the final desired product. When the generated water is not removed, the yield of the final product is low.

It is known that the condensation reaction of m-hydroxybenzene and bromobenzene readily proceeds in the absence of solvent by using an excess of bromobenzene. However, in the process of this invention, the yield of the final product is low even when the solvent is not used but chlorobenzene is used in excess and the reaction is carried out while removing the generated water as an azeotrope with chlorobenzene under reflux at temperatures near the boiling point (131°–132° C.) of chlorobenzene.

In a condensation reaction using a phenol, water is usually removed by adding a non-aqueous solvent such as toluene to a mixture of the phenol and a base and heating the mixture to the azeotropic temperature, and after adding the catalyst, halobenzene and solvent, the reaction is started. This method, however, cannot give the desired yield in the production of m-phenoxybenzyl alcohol.

In the process of this invention, therefore, the reaction temperature is important, and should be at least 140° C. If, however, it exceeds 200° C., the starting m-hydroxybenzyl alcohol decomposes, and the selectivity of m-phenoxybenzyl alcohol decreases. Accordingly, the reaction temperature should be maintained at 140° to 200° C. In the present invention, a polar solvent having a higher boiling point than chlorobenzene is used so that the reaction can be carried out at a reaction temperature higher than the boiling point of chlorobenzene. During the reaction, azeotropic dehydration is carried out while refluxing chlorobenzene.

Any solvents which are inert to the reaction and have higher boiling points than chlorobenznee can be used as the polar solvent in the present invention. Examples of preferred polar solvents for use in the process of this invention are N,N'-dimethylimidazolidinone, N,N-dimethylformamide, dimethyl sulfoxide, N-methyl-2-pyrrolidone and sulfolane. The preferred amount of the polar solvent is 1 to 10 times the weight of m-hydroxybenzyl alcohol.

If the amount of chlorobenzene is too large as compared with the polar solvent, the reaction temperature does not rise and the rate of the reaction becomes slow. If it is too small, dehydration as a chlorobenzene azeotrope does not take place efficiently, and the selectivity of m-phenoxybenzyl alcohol decreases. The amount of chlorobenzene is, therefore, slightly in excess of one equivalent to m-hydroxybenzyl alcohol, and preferably 1.2 to 3.0 moles per mole of m-hydroxybenzyl alcohol, and 0.05 to 4.0 times, preferably 0.2 to 1.0 time, the weight of the polar solvent. After the reaction, the solvent can be recycled for reuse in a usual manner such as distillation.

By carrying out the process of this invention, m-phenoxybenzyl alcohol can be obtained in a high yield even by the use of chlorobenzene as the halobenzene. Of course, bromobenzene may be permissibly used in place of chlorobenzene, and in this case, too, the product can be obtained in a high yield.

The following examples illustrate the process of this invention more specifically.

EXAMPLE 1 m-Hydroxybenzyl alcohol (50.0 g; 0.40 mole), 90.0 g (0.80 mole) of chlorobenzene, 156.6 g (1.37 moles) of N,N'-dimethylimidazolidinone and 41.8 g (0.30 mole) of potassium carbonate were mixed, and 0.8 g of cuprous chloride and 1.2 g of 8-hydroxyquinoline were added. The mixture was heated to 150° C. in an inert gaseous atmosphere. The mixture was stirred for 17 hours while continuing refluxing and dehydration. During this time, the reaction temperature gradually rose and reached 162° C. at the end of 17 hours. The mixture was further heated to 170° C., and stirred for 3 hours at this temperature.

After the reaction, the reaction mixture was cooled and 200 ml of 5% cold dilute sulfuric acid was added. The mixture was extracted with ether, and the ethereal layer was washed with a saturated aqueous solution of sodium bicarbonate and a saturated aqueous solution of sodium chloride, and dried over anhydrous sodium sulfate. GLC analysis showed that the conversion of m-hydroxybenzyl alcohol was 100%, the selectivity of m-phenoxybenzyl alcohol was 93%, and the yield of m-phenozybenzyl alcohol was 93%.

The ether was then evaporated, and the residue was distilled under reduced pressure to give purified m-phenoxybenzyl alcohol (boiling point 170°–174° C., 9 mmHg; amount yielded 72.1 g; the yield of the isolated product: 90%).

EXAMPLE 2

Example 1 was repeated except that 165.0 g of dimethyl sulfoxide was used instead of 156.6 g of N,N'-dimethylimidazolidinone as the polar solvent. GLC analysis of the resulting reaction mixture showed that the conversion of m-hydroxybenzyl alcohol was 99%, the selectivity of m-phenoxybenzyl alcohol was 91%, and the yield of m-phenoxybenzyl alcohol was 90%.

COMPARATIVE EXAMPLE 1

Example 1 was repeated except that water in the reflux system was not removed out of the system. GLC analysis of the reaction mixture showed that the conversion of m-hydroxybenzyl alcohol was 35%, the selectivity of m-phenoxybenzyl alcohol was 74%, and the yield of m-phenoxybenzyl alcohol was 26%.

COMPARATIVE EXAMPLE 2

Example 1 was repeated esxcept that N,N'-dimethylimidazolidinone as the polar solvent was not used, the amount of chlorobenzene used was increased to 300.0 g, and the reaction was carried out for 24 hours under reflux (130° to 132° C.) while performing azeotropic dehydration. GLC analysis of the reaction mixture showed that the conversion of m-hydroxybenzyl alcohol was 70%, the selectivity of m-phenoxybenzyl alcohol was 71%, and the yield of m-phenoxybenzyl alcohol was 50%.

What is claimed is:

1. Process for producing m-phenoxybenzyl alcohol which comprises reacting chlorobenzene with m-hydroxybenzyl alcohol in the presence of a catalytic amount of a copper complex of 8-hydroxyquinoline and a base, wherein chlorobenzene is added to a polar solvent having a higher boiling point that chlorobenzene, the amount of chlorobenzene being 0.05 to 4.0 times the weight of the polar solvent; at least one compound selected from the group consisting of alkali hydroxides, alkali carbonates and alkali bicarbonates, is used as the base in an amount of 1.0 to 2.0 gram-equivalents per mole of m-hydroxybenzyl alcohol; and the reaction is carried out at a temperature of 140° to 200° C. while removing the generated water as an azeotrope with chlorobenzene.

2. The process of claim 1 wherein the polar solvent is N,N'-dimethylimidazolodinone, N,N'-dimethylformamide, dimethyl sulfoxide, N-methyl-2-pyrrolidone or sulfolane.

3. The process of claim 1 wherein the polar solvent is used in an amount 1 to 10 times the weight of m-hydroxybenzyl alcohol.

* * * * *